(12) United States Patent
Lapham

(10) Patent No.: US 6,442,451 B1
(45) Date of Patent: Aug. 27, 2002

(54) VERSATILE ROBOT CONTROL SYSTEM

(75) Inventor: John R. Lapham, Fort Myers, FL (US)

(73) Assignee: Robotic Workspace Technologies, Inc., Fort Myers, FL (US)

( * ) Notice: Subject to any disclaimer, the term of this patent is extended or adjusted under 35 U.S.C. 154(b) by 41 days.

(21) Appl. No.: 09/750,433

(22) Filed: Dec. 28, 2000

(51) Int. Cl.[7] ............................................ G06F 19/00
(52) U.S. Cl. .................. 700/245; 700/247; 700/248; 700/249; 700/259; 700/260; 318/568.11; 318/568.13; 318/568.16; 318/573; 318/574; 701/23; 701/24; 901/2; 901/8; 901/16; 901/47
(58) Field of Search ................................. 700/257, 245, 700/249, 251, 259, 260, 264, 86, 247, 248, 96; 318/568.11, 568.16, 568.15, 568.19, 568.13, 574, 573; 901/2, 8, 47, 16; 345/764; 701/23, 24; 710/8, 62, 64

(56) References Cited

U.S. PATENT DOCUMENTS

| | | | |
|---|---|---|---|
| 4,218,757 A | * | 8/1980 | Drogichen ............... 264/297.2 |
| 4,586,151 A | * | 4/1986 | Buote ......................... 370/259 |
| 4,589,063 A | * | 5/1986 | Shah et al. ................. 711/112 |
| 4,689,755 A | * | 8/1987 | Buote ........................... 703/23 |
| 4,730,258 A | * | 3/1988 | Takeda et al. ................ 706/10 |
| 4,831,549 A | * | 5/1989 | Red et al. .................... 382/209 |
| 4,891,529 A | * | 1/1990 | Braun et al. ................. 701/301 |
| 4,954,762 A | * | 9/1990 | Miyake et al. ........... 219/124.34 |
| 4,974,191 A | * | 11/1990 | Amirghodsi et al. ........ 345/700 |
| 5,008,834 A | * | 4/1991 | Mizuno et al. ............. 700/245 |
| 5,038,089 A | * | 8/1991 | Szakaly ...................... 318/573 |
| 5,329,450 A | * | 7/1994 | Onishi .................... 318/568.15 |
| 5,825,981 A | * | 10/1998 | Matsuda ................ 318/568.16 |

FOREIGN PATENT DOCUMENTS

| | | | |
|---|---|---|---|
| EP | 0 007 028 A1 | * | 1/1980 |
| EP | 0 180 926 A2 | * | 5/1986 |

\* cited by examiner

*Primary Examiner*—William A. Cuchlinski, Jr.
*Assistant Examiner*—McDieunel Marc
(74) *Attorney, Agent, or Firm*—Olson & Hierl, Ltd.

(57) ABSTRACT

An improved, versatile robot control system comprises a general purpose computer with a general purpose operating system in electronic communication with a real-time computer subsystem. The general purpose computer includes a program execution module to selectively start and stop processing of a program of robot instructions and to generate a plurality of robot move commands. The real-time computer subsystem includes a move command data buffer for storing the plurality of move commands, a robot move module linked to the data buffer for sequentially processing the moves and calculating a required position for a robot mechanical joint. The real-time computer subsystem also includes a dynamic control algorithm in software communication with the move module to repeatedly calculate a required actuator activation signal from a robot joint position feedback signal.

32 Claims, 4 Drawing Sheets

VERSATILE ROBOT CONTROL SYSTEM

FIELD OF THE INVENTION

This invention relates to an apparatus and method for controlling a robot, and more particularly, to a versatile control system suitable for controlling robots of various electromechanical configurations.

COPYRIGHT NOTIFICATION

Portions of this patent application contain materials that are subject to copyright protection. The copyright owner has no objection to the facsimile reproduction by anyone of the patent document, or the patent disclosure, as it appears in the Patent and Trademark Office.

BACKGROUND OF THE INVENTION

Industrial robots and similar highly flexible machine tools gained commercial acceptance during the late 1970s. Since then, the use of industrial robots has only increased, particularly for automobile manufacturing.

The guiding purpose for industrial robots is manufacturing flexibility. Robots allow assembly lines and work cells to make different articles with no or minimal manual equipment changes. The list of robot applications in manufacturing is long and ever increasing. Examples include computer vision inspection, spot and arc welding, spray painting, drilling, part placement, and adhesive application.

The boundary between robots and machine tools is not strictly defined. Compared with conventional machine tools, robots generally have more joints (or axes) of motion thereby offering more degrees of freedom for positioning an end effector. In the robotics field, the term "end effector" has been adopted to cover the variety of active equipment carried by robots. Such equipment varies according to the manufacturing application, e.g. spot welding.

Robots generally include positioning arms with mechanical joints, actuators such as motors for causing movement about the joints, and sensors which aid in determining the position (or pose) of the robot. Although most include these core components, industrial robots new and old otherwise vary greatly in their electromechanical configurations.

For example, some robots rely only on revolute, (i.e. rotary) joints, while some are equipped with combinations of linear and revolute axes. Robots with a series of extending arms and revolute joints have been labeled articulating robots.

Even among a given class of robots there is mechanical variation. The revolute joints of articulating robots may be, for example, offset from their supporting arm—a shoulder joint, centered to the supporting arm—an elbow joint or axially aligned with the supporting arm—a wrist joint. Likewise, linear joints may be co-linear or orthogonal. Actuators and feedback sensors are another source of the varying configurations. For example; some robots are equipped with stepper motors, others servo motors.

Electronic control systems are employed to control and program the actions of robots. For the necessary coordinated action between the end effector and the robot positioning, robot control systems preferably provide some level of software programming and an interface to field I/O and end effector subsystems. Conventional robot control systems are collections of customized electronics that vary according to robot configuration and robot manufacturer.

In manufacturing processes, robots are directed by a list of control instruction to move their end effector through a series of points in the robot workspace. The sequence (or program) of robot instructions are preferably maintained in a non-volatile storage system (e.g. a computer file on magnetic-disk).

Manufacturing companies, the robot users, through their engineers and technicians, have come to demand two important features from manufacturing control systems. First, robot users seek control systems implemented using commercially standard computers and operating systems rather than customized proprietary systems. This trend toward the use of commercially standard computer hardware and software has been labeled the "open systems movement."

Control systems based on standard computers are preferred because they offer robot users simplified access to manufacturing data via standard networks and I/O devices (e.g. standard floppy drives), the ability to run other software, and a competitive marketplace for replacement and expansion parts. Underlying the open systems movement is the goal of reducing robot users' long-term reliance on machine tool and robot manufacturers for system changes and maintenance.

A second feature sought by robot users is a common operator and programmer interface for all robots, facility (if not company) wide. A common user interface for all robots reduces the need for specialized operator training on how to use the customized proprietary systems.

With respect to the open-systems feature, efforts at delivering a robot control system based on standard, general purpose computer systems have not been fully successful because of the limitations of general purpose operating systems. Robot safety and accuracy requirements dictate that robot control systems be highly reliable, i.e. crash resistant, and tied to real-time. The multi-feature design objectives for general purpose operating systems such as Microsoft Windows NT® have yielded very complex, somewhat unreliable software platforms. Moreover, such systems cannot guarantee execution of control loops in real-time.

With respect to the common operator interface features, attempts to offer even limited standards to operator interfaces have not extended beyond a specific robot manufacturer. Notwithstanding the difficulty in getting different robot manufacturers to cooperate, the wide variety of electromechanical configurations has heretofore substantially blocked the development of robot control systems with a common operator interface.

Accordingly, it would be desirable to provide an improved robot control system that both employs commercially standard computer systems and accommodates robots of different configurations. Specifically, it would be desirable to provide the advantages of open systems and a common operator interface to robot control.

SUMMARY OF THE INVENTION

Robot control systems of the present invention provide robot control via commercially standard, general purpose computer hardware and software. The control systems and methods according to the present invention are usable with robots of varying electromechanical configurations thereby allowing a common operator interface for robots from different robot manufacturers.

The present invention provides a control system for running or processing a program of robot instructions for robots equipped with a mechanical joint, a mechanical actuator to move the joint and a position feedback sensor. The robot mechanical actuators receive an activation signal and the feedback sensor provides a position signal.

A control system according to the present invention includes a general purpose computer with a general purpose operating system and a real-time computer subsystem in electronic communication with the general purpose computer and operably linked to the mechanical actuator and the position feedback sensor. The general purpose computer includes a program execution module to selectively start and stop processing of the program of robot instructions and to generate a plurality of robot move commands.

Within the real-time computer system is a move command data buffer for storing a plurality of move commands. The real-time computer subsystem also includes a robot move module and a control algorithm. The move module is linked to the data buffer to sequentially process the plurality of move commands and calculate a required position for the mechanical joint. The control algorithm is in software communication with the robot move module to repeatedly calculate a required activation signal from the feedback signal and the required position for the mechanical joint.

Another aspect of the present invention provides a robot control system suitable for controlling robots of different electromechanical configurations. The control system includes a robot-independent computer unit in electronic and software communications with a robot-specific controller unit.

The robot-independent computer unit is operably linked to the robot by an I/O interface and includes a video display and a first digital processor running an operator interface module for creating a sequence of robot move commands. The robot-specific controller unit includes a second digital processor running a real-time tied operating system and a robot move module for executing the robot move commands.

The operator interface module preferably includes a configuration variable for storing data defining the electromechanical configuration of the robot, a first code segment for generating a first operator display according to a first electromechanical configuration, a second code segment for generating a second operator display according to a second electromechanical configuration, and a third code segment for selecting the first or second code segment according to the electromechanical configuration.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
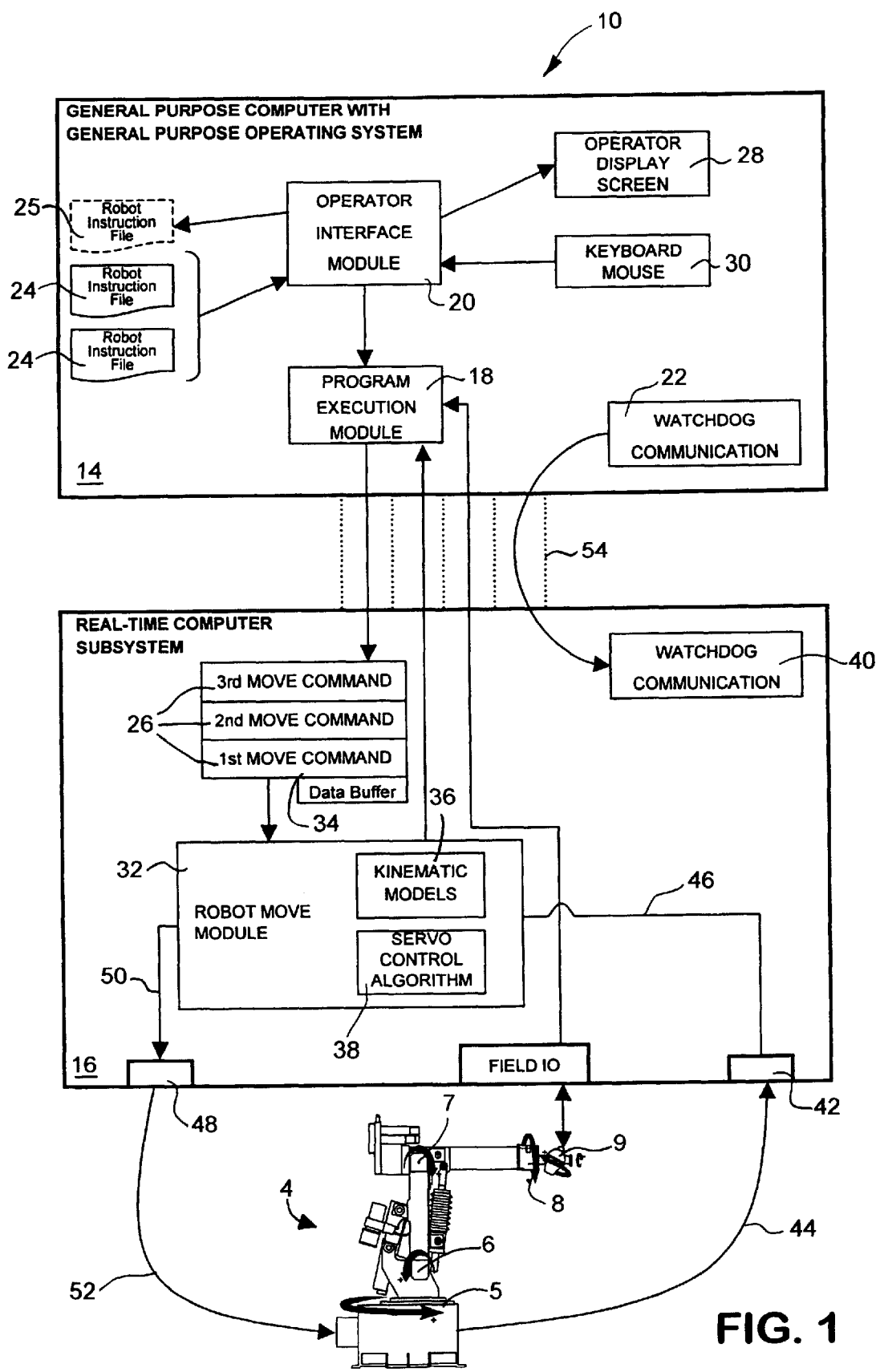
FIG. 1 is schematic block diagram illustrating the software programs, computer hardware and robot connections of a robot control system according to the present invention.

The invention disclosed herein is, of course, susceptible of embodiment in may different forms. Shown in the drawings and described herein below in detail are preferred embodiments of the invention. It is to be understood, however, that the present disclosure is an exemplification of the principles of the invention and do not limit the invention to the illustrated embodiments.

In the FIGURES, a single block or cell may indicate several individual software and/or hardware components that collectively perform the identified single function. Likewise, a single line may represent several individual signals or several instances of software data sharing or interconnection.

Robots as well as other manufacturing machines include positioning arms with mechanical joints, positioning actuators such as motors for causing movement about the joints, and position feedback sensors which provide an indication the position of some part of the robot. As used herein, the term "mechanical actuator" is a reference to the variety of devices used for robot motion. Exemplary robot actuators are hydraulic pistons, pneumatic pistons, servo motors, stepper motors and linear motors.

Referring to FIG. 1, the elements of a control system 10 are shown with an industrial robot 4, a Cincinnati Milacron 776 robot. Robot 4 includes a series of revolute joints 5, 6, 7 and 8, corresponding servo motors and an end effector 9. Control system 10 includes a general purpose computer 14 and a real-time computer subsystem 16.

The phrase "general purpose computer," as used herein, is a reference to commercially standard computers which are designed for multiple applications as opposed to CPU-based electronics customized for a specific application such as device control. Examples include the well-known group of computers conventionally labeled IBM-compatible personal computers, or more simply PCs. PCs are based on complex instruction set (CISC) CPUs from Intel Corporation (INTEL), Advanced Micro Devices, Inc. (AMD) and VIA Technologies, Inc. The related, evolving CPU product line from INTEL includes CPU chipsets available under the designations "80486®," "Pentium®," "Pentium® II," "Pentium® III." An exemplary CPU product line for general purpose computers by AMD is available under the designation "AMD-K6®." VIA Technologies, Inc. CPUs for general purpose computers are sold under the designation "Cyrix®."

General purpose computers based on reduced instruction set (RISC) CPUs are also well known. Examples include computers based on the Alpha® chipset available from the Compaq Computer Corporation.

As indicated in FIG. 1, general purpose computer 14 operates with a general purpose operating system. The phrase "general purpose operating system" is a reference to commercially standard operating systems such as those available from the Microsoft Corp. under the designations MS-DOS®, Windows 95®, Windows 98®, Windows® NT and Windows 2000®. Other examples of general purpose operating systems include Macintosh® (Apple Computers, Inc.), UNIX (various resellers), Open VMS® (Compaq Computer Corporation).

Installed for running on the general purpose computer are a program execution module 18, an operator interface module 20, and watchdog communication code segments 22. The term "module," as used herein is a reference to a software element such as a program, subprogram, software process, subroutine, or grouping of code segments and the like. The software modules of control system 10 are preferably discrete executable programs which run as discrete processes. Unless otherwise indicated, the software modules and code segments are configured to share access to a variety of software variables and constants as needed through subroutine calls, common shared memory space, and the like.

Program execution module 18 processes programs of robot instructions 24, which can be stored as data files as represented in FIG. 1. From robot instruction programs 24, program execution module 18 generates robot move commands 26 for delivery to real-time computer subsystem 16. Via execution module 18, the relatively more human readable robot instructions 24 generated by a robot operator are interpreted and translated into move commands 26 for real-time computer subsystem 16.

As well, program execution module 18 allows operator control of the running of robot programs 24 by selectively starting and stopping the transfer of move commands 26 to real-time computer subsystem 16 in response to prompts from the operator via operator interface module 20.

Operator interface module 20 is operably linked to an operator display screen 28, a keyboard and/or mouse 30, and other standard peripherals as desired. In a preferred embodiment, display screen 28 is a touch screen which allows a robot operator to input prompts and data through both displays and keyboard/mouse 30.

With robot operator prompts and selections, operator interface module 20 allows robot instruction files 24 to be loaded from disk and processed (or executed) by program execution module 18 for controllably moving robot 4. Operator interface module 20 generates operator screens and accepts from the operator numeric data and prompts. Numeric data entries are communicated to other program modules as necessary. Prompts by the robot operator to start and stop the running of a robot program are received by operator interface module 20 and forwarded to execution module 18.

In addition to accepting operator inputs for loading, starting and stopping programs 24, operator interface 20 preferably includes an editor for use by an operator to generate new programs of robot instructions 25. Because the present invention provides a control system which relies upon general purpose computers such as a Windows NT PC, it is equally possible to generate robot programs on another PC such as an office PC and then transfer the file to general purpose computer 14 through standard peripherals such as disk drives or computer network connections.

General purpose computer 14 is electronically linked for data exchange (i.e. communication) with real-time computer subsystem 16. Real-time computer subsystem 16 preferably includes a hardware, firmware and software combination designed for process control applications. As opposed to general purpose computers with general purpose operating systems, real-time computers provide for substantially uninterruptible execution of calculations required for a plurality of control loops with relatively fast cycle times (e.g. 0.5–2 msec).

Because of the extensive signal processing requirements, the CPU computer of real-time computer subsystem 16 is preferably a DSP-based computer. In this category of DSP-based control computers, the systems commercially available from Delta Tau Data Systems, Inc. (Chatsworth, Calif.) under the designations "PMAC", "PMAC2," "Turbo PMAC" and "UMAC" are presently preferred.

Real-time computer subsystem 16 includes a robot move module 32, a move command data buffer 34, kinematic models 36, servo control algorithms 38, and watchdog intercommunication code segments 40. Real-time subsystem 16 also includes I/O hardware and software drivers to provide an operable link to the positioning related electronics of robot 4. Represented by block 42 are the hardware and software components necessary for receiving and translating robot feedback signals 44 into computer data feedback signals 46. Likewise, block 48 represents the components necessary for converting computer data setpoints 50 into actuator-appropriate activation signals 52.

Activation signals 52 and feedback signals 44 may be analog signals, digital signals or combinations of both depending upon the configuration of robot 4. For example, the typical motor-with-amplifier actuator calls for an analog activation signal. Newer, so-called "smart" devices can be directly activated by digital signals, however. Thus, the type of signal conversion performed by I/O systems 42 and 48 varies by robot configuration.

Robot move module 32 is resident in real-time computer subsystem 16 to accept move commands 26 and feedback signals 44/46 to generate the necessary activation signals 50/52. Robot move module 32 relies upon kinematic models 36 and servo control algorithms 38 to translate move commands 26 required joint positions and then appropriate activation signal setpoints 50. In a preferred embodiment of the present invention, move commands 26 are expressed as changes in joint position or as changes in end-effector position.

Move commands based on joint position rely upon a predefined range on a one-dimensional joint axis model, for example, +90 degrees to −90 degrees for a revolute axis and 0 to 1200 millimeters (mm) for a linear joint. An example of a move command based on joint position is "set joint one at 60 degrees." In a preferred embodiment of the present invention, robot move module 32 is programmed to accept joint move commands as a function call specifying the position of all robot mechanical joints 5, 6, 7 and 8, thereby allowing only one or all joints to be moved.

Move commands expressed as end-effector positions rely upon a predefined, but customary, three-dimensional coordinate system for locating the end-effector. A move command based on end-effector position is a call to move the end effector to a point in the end-effector's workspace.

For joint position move commands, robot move module 32 includes software models for translating data from feedback signals 46 into joint position. The required calculation varies according to joint type and the type feedback signal available. For example, a feedback sensor directly measuring an indication of joint position require limited translation, while a feedback sensor measuring the number of rotations of a positioning motor may require a more complex translation.

To process move commands based on end-effector position, robot move module 32 additionally includes a kinematic model for calculating the required position of joints 5, 6, 7 and 8, given a desired position for end effector 9.

More specifically, real-time computer subsystem 16 uses kinematic model algorithms for computation of the forward and inverse kinematics of the robot. Forward kinematics computation refers to the determination of end-effector position and orientation given known joint positions or actuator positions of the robot. Inverse kinematics is the determination of the joint angle or actuator positions given an end-effector position.

The required combination of individual joint axes models and overall kinematics models is represented in FIG. 1 by block 36. Kinematic algorithms are described in other patents and the technical literature. See, for example, Chapters 3 and 4 of Craig, John J. *Introduction to Robotics: Mechanics and Control,* 2nd Ed., Addison-Wesley, 1989. The specific models employed vary according to the electromechanical configuration of the robot to be controlled.

Because the positioning actuator and feedback sensor combination make up a dynamic system, real-time computer subsystem 16 also includes control algorithms 38 to provide the required dynamic calculations. Preferred among available closed loop servo motor control schemes is a proportional-integral-derivative (PID) with feedforward algorithm.

Data buffer 34 is a software variable available to programs in both general purpose computer 14 and real-time computer subsystem 16 for storing multiple move commands 26 received from program execution module 18. Although the desired storage capacity for data buffer 34 can vary, in a preferred embodiment of the present invention data buffer 34 and connected modules are preferably configured such that from 2 to 10, and more preferably from 3 to 4, move commands are stored.

With move command data buffer 34, control system 10 provides for substantially continuous, uninterrupted control of robot 4 even in response to program execution delays in general purpose computer 14.

As noted above, general purpose computers running general purpose operating systems are relatively unreliable, exhibiting unpredictable control program interruption. Specific motion control of robot 4 by real-time computer subsystem 16 is not affected by unpredictable delays in operations of general purpose computer 14 because robot move module 32 can continue to draw move commands 26 from data buffer 34.

Although a variety of data transfer mechanisms are available to provide electronic and software-level communication between general purpose computer 14 and real-time computer subsystem 16, a commercially standard data bus backplane is preferred. The data bus connection is symbolically represented in FIG. 1 by reference numeral 54. The ISA bus, the PCI bus, and the VME bus are exemplary standard data buses, with the ISA bus being presently preferred.

For convenient space-saving connection to data bus 54, the computer mother board portions of general purpose computer 14 and real-time computer subsystem 16 are data bus cards. As used herein, the term "bus card" is a reference to printed circuit boards with electronic components and a tab with a plurality of contacts that is received in the card slots of a data bus chassis. The DSP real-time computers available from Delta Tau Data Systems, Inc. noted above are available as ISA data bus cards.

Figure 2:
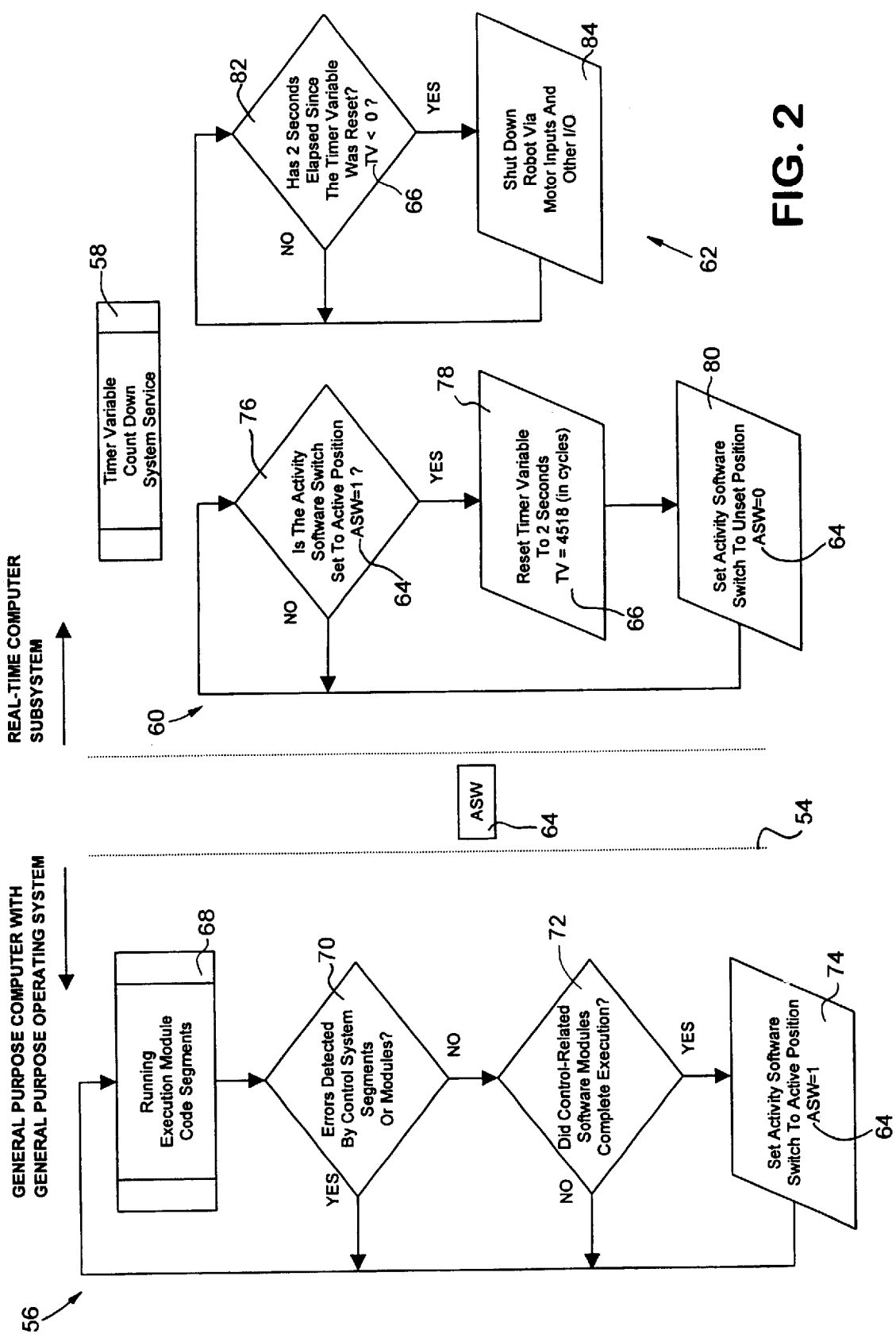
FIG. 2 is simplified flowchart of a preferred embodiment of software and method steps for providing the watchdog intercommunication between the general purpose computer and the real-time computer subsystem.

In a preferred embodiment, control system 10 includes a security (or "watchdog") communication (blocks 22 and 40) between general purpose computer 14 and real-time computer subsystem 16. Flowchart FIG. 2 shows the preferred code segments for maintaining the watchdog management. As illustrated, a preferred watchdog scheme includes code segments operating in both general purpose computer 14 and real-time computer subsystem 16. Resident in general purpose computer 14 is a status code segment 56 and resident in the real-time computer subsystem are a timer code segment 58, a timer reset code segment 60, and a fail safe code segment 62.

The code segments interact with two software variables: an activity software switch (ASW) 64 for indicating whether programs in general purpose computer 14 are active and/or error free, and a timer variable (TV) 66 for storing an elapsed time indication. Timer variable 66 is resident in real-time computer subsystem 16 while activity software switch 64 is shared via data bus 54 or other means. Activity software switch 64 is implemented as an integer software variable with an unset position being represented by zero and a set, or active position, being represented by one.

Status code segment 56 optionally, but preferably, runs sequentially with program execution module 18 (box 68) and repeatedly sets activity software switch 64 to the active position (box 74). After the completion of a run cycle of program execution module 18, status code segment 56 examines other software variables which indicate special errors (box 70) or delays in the processing of other programs (box 72) in the general purpose computer 14. Accordingly, if program execution module 18 is interrupted or if errors or other delays are detected, activity switch 64 is not set.

Timer code segment 58 counts down timer variable 66 according to elapsing time. Timer code segment 58 is preferably a system service function of real-time computer subsystem 16 and expressed in execution cycles.

When the activity software switch is in the active position (box 76), timer reset code segment 60 repeatedly resets the timer variable to a predetermined amount of time (box 78; preferably two seconds) and repeatedly sets the activity software switch back to the unset position (box 80). Fail safe code segment 62 responds to an overrun of timer variable 66 (box 82) by shutting down robot 4 via activation signals 50/52 and other robot I/O.

Acting together, code segments 56, 58, 60 and 62, provide a watchdog service which will shut down robot 4 if the operation of general purpose computer 14 is stopped or delayed for more than two seconds.

Referring back to FIG. 1, another feature of the present invention is that the software provided for general purpose computer 14 is suitable for controlling robots of various electromechanical configurations. According to this aspect of the invention, general purpose computer 14 serves as a robot-independent computer unit while real-time computer subsystem 16 serves as a somewhat robot-specific controller unit, or customized interface or adapter to the robot.

Figure 3:
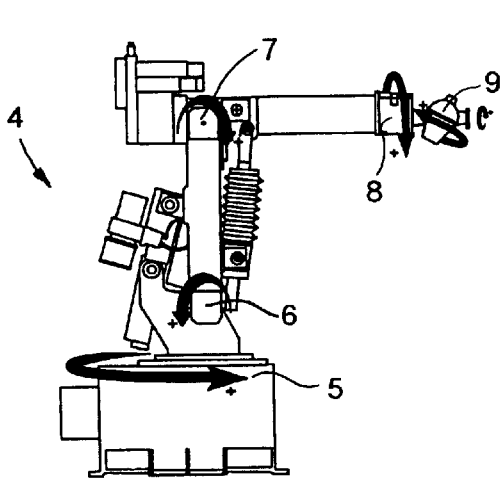
FIG. 3 is a side elevation view of an articulating industrial robot illustrating another type of robot configuration controllable by embodiments of the present invention.
Figure 4:
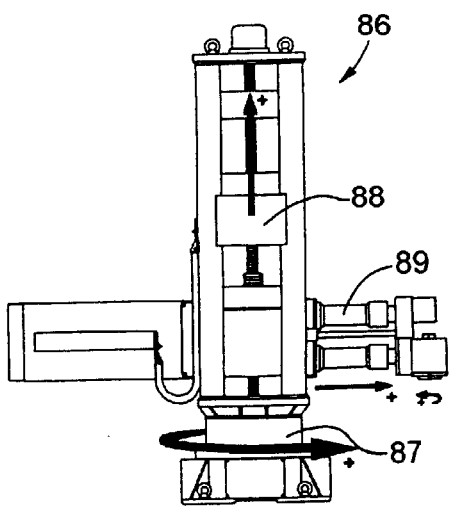
FIG. 4 is a side elevation view of an industrial robot equipped with linear joints and illustrating one of the many types of robot configurations controllable by embodiments of the present invention.

Important to the multi-configuration aspect of the present invention is the enhanced versatility of operator interface module 20. Viewed together, FIGS. 3 and 4 demonstrate the challenge of working with robots of different electromechanical configurations. FIG. 3 is side view of articulating robot 4 from FIG. 1 in slightly larger scale to reveal greater detail. The arms of robot 4 are connected by a series of revolute (or rotary) joints 5, 6, 7 and 8. In contrast, FIG. 4 is side view of a robot 86 which is equipped with a revolute, torso joint 87 and two linear joints 88 and 89.

Assigning joint numbers from the base up, the second and third joints of robot 4 are of a different type than the second and third joints of robot 86. To overcome this difference in configuration, the operator interface of the present invention includes a configuration variable for storing data specifying the electromechanical configuration of the robot and display generating code segments for each type of configuration.

In a preferred embodiment, the configuration variable is defined and/or sized to store data defining the type of robot joint, linear or revolute, and whether a specified revolute joint is windable, i.e. capable of turning more than 360 degrees.

Figure 5:
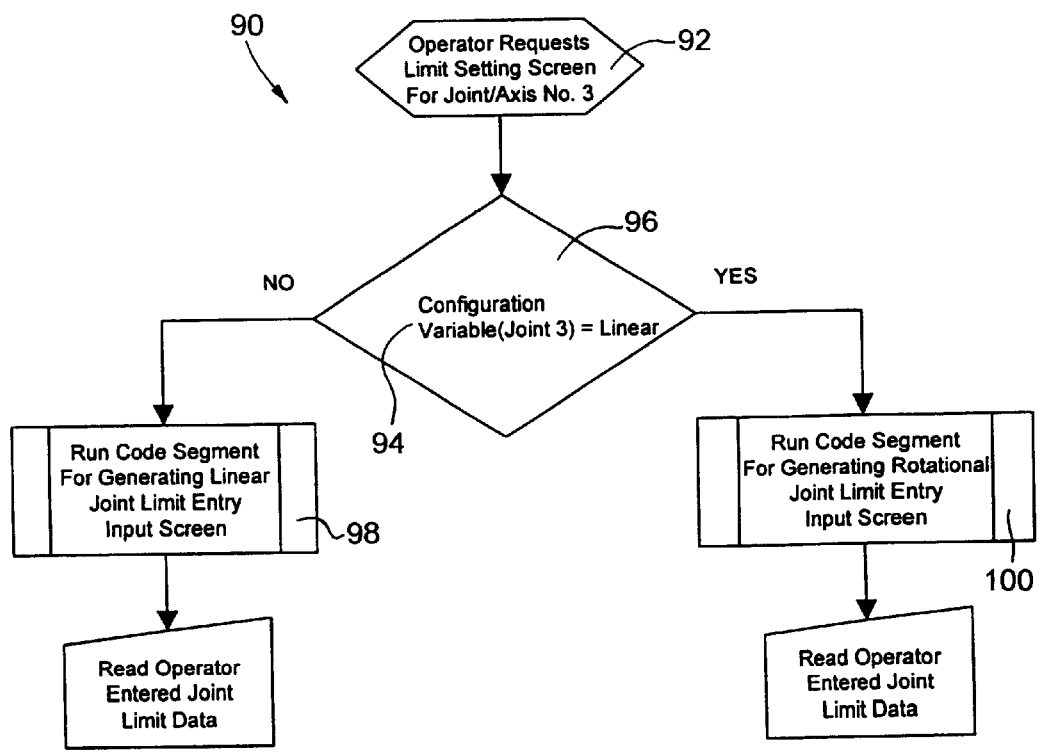
FIG. 5 is a simplified flow chart of preferred software and method steps for accommodating robots of different electromechanical configurations and demonstrating the role of the configuration variable in control systems according to the present invention.
Figure 6:
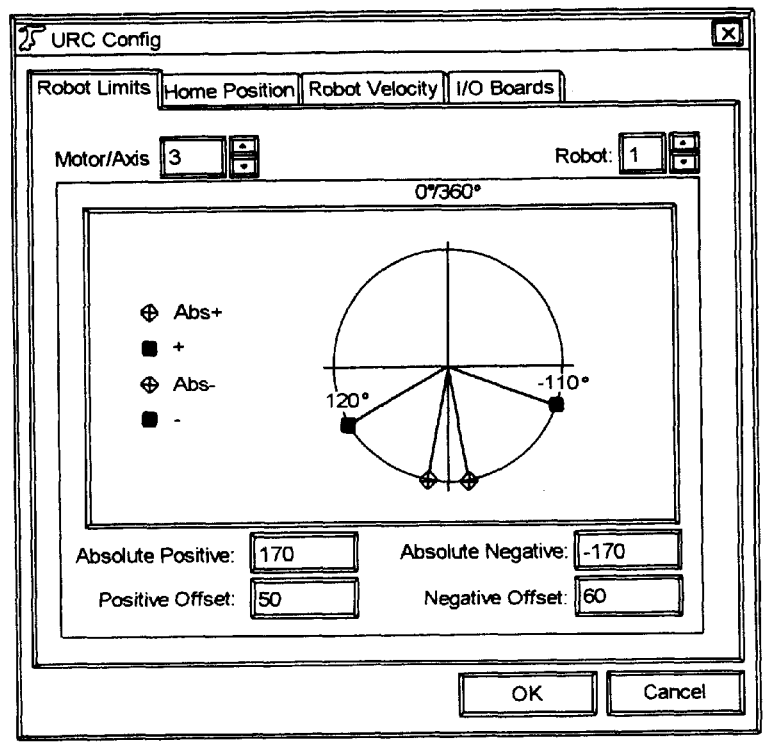
FIG. 6 is likewise an exemplary operator interface display screen generated in response to data stored in the configuration variable specifying a rotational joint configuration.
Figure 7:
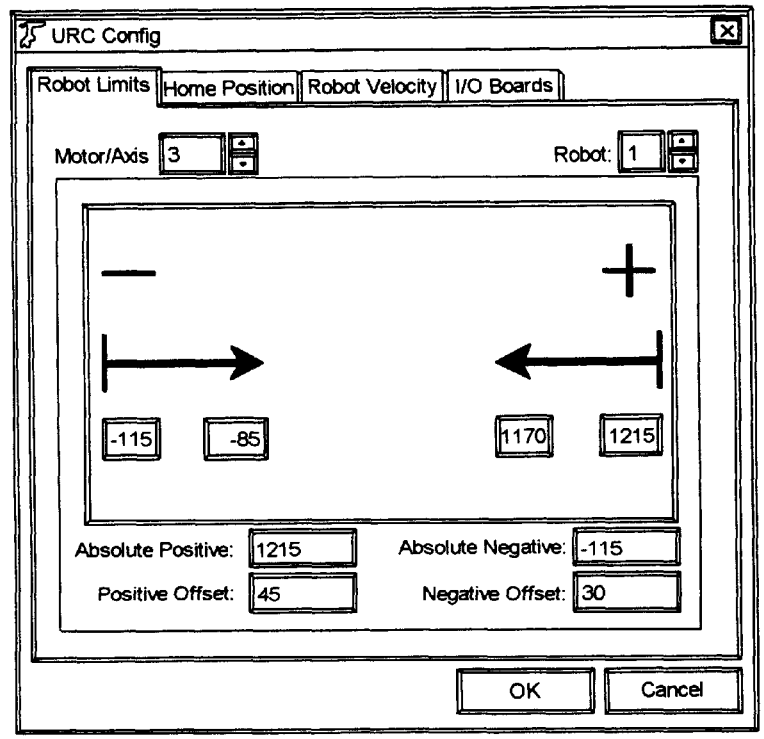
FIG. 7 is an exemplary operator interface display screen generated in response to data stored in the configuration variable specifying a linear joint.

FIGS. 5 through 7 provide an example of how operator interface module 20 uses the configuration variable to accommodate different types of robots. As illustrated in FIG. 5, a display selecting code segment 90 responds to an operator request to set limits for joint/axis 3 (box 92). Code segment 90 checks in configuration variable 94 for data specifying whether joint 3 is linear or revolute (box 96).

Depending upon whether the third joint of the robot to be controlled is revolute as with robot 4 or linear as with robot 86, code segment 90 selects one of two available displays for setting joint limits. For a revolute joint type, box 98 is selected and the revolute joint/axis display of FIG. 6 is generated at screen 28. For a linear joint type, box 100 is selected and the linear joint/axis display of FIG. 7 is generated.

The foregoing specification and drawings are to be taken as illustrative but not limiting of the present invention. Still other configurations and embodiments utilizing the spirit and scope of the present invention are possible, and will readily present themselves to those skilled in the art.

I claim:

1. A control system for processing a program of robot instructions for robots having a mechanical joint, a mechanical actuator to move the joint and a position feedback sensor, the mechanical actuator being adapted to receive an activation signal and the feedback sensor providing a position signal, the control system comprising:
   a general purpose computer with a general purpose operating system, said general purpose computer including a program execution module to selectively start and stop processing of the program of robot instructions and to generate a plurality of robot move commands; and
   a real-time computer subsystem in electronic communication with said general purpose computer and operably linked to the mechanical actuator and the position feedback sensor, a move command data buffer for storing said plurality of move commands, a robot move module linked to said data buffer to sequentially process said plurality of move commands and calculate a required position for the mechanical joint, and a control algorithm in software communication with said robot move module to repeatedly calculate a required activation signal from a position signal and said required position for the mechanical joint.

2. The control system according to claim 1 further comprising a watchdog intercommunication between said real-time computer subsystem and said general purpose computer for detecting faults in operation of said general purpose computer.

3. The control system according to claim 2 wherein said watchdog intercommunication includes:
   a timer variable for storing an elapsed time indication;
   a timer code segment for adjusting said timer variable according to passing time;
   an activity software switch having an active position and an unset position;
   a status code segment installed in said general purpose computer for repeatedly setting said activity software switch to said active position;
   a timer reset code segment installed in said real-time computer subsystem for repeatedly resetting said timer variable to a predetermined amount of time when said activity software switch is in said active position and repeatedly setting said activity software switch to said unset position; and
   a fail safe code segment installed in said real-time computer subsystem for repeatedly inspecting said timer variable and setting said activation signal to shut down the robot if said timer variable reaches a predetermined value.

4. The control system according to claim 3 wherein said activity software switch is implemented as an integer software variable with said unset position being represented by zero and said active position being represented by one.

5. The control system according to claim 1 further comprising a data bus for receiving bus cards and wherein said real-time computer subsystem includes a bus card with a central processing unit, said bus card being installed in said data bus.

6. The control system according to claim 1 wherein said general-purpose computer and said real-time computer subsystem are electronically linked via a standard data bus.

7. The control system according to claim 1 wherein said general-purpose computer and said real-time computer subsystem are electronically linked via an ISA data bus.

8. The control system according to claim 1 further comprising a data bus for receiving bus cards and wherein said real-time computer subsystem includes a first bus card with a central processing unit and said general purpose computer includes a second bus card with a central processing unit, both said first and said second bus cards being installed in said data bus.

9. The control system according to claim 1 wherein said real-time computer subsystem includes a digital signal processor (DSP) based computer.

10. The control system according to claim 1 wherein said general purpose computer is an Intel Pentium® processor based computer.

11. The control system according to claim 1 wherein said general purpose computer is a DEC/Compaq Alpha® processor based computer.

12. The control system according to claim 1 wherein said general purpose operating system is a not tied to real-time.

13. The control system according to claim 1 wherein said general purpose operating system is a member of the group consisting of a Windows-NT®, a Windows 2000®, a Windows 95®, a Windows 98®, an Open VMS®, a PC/MS DOS, and a Unix.

14. The control system according to claim 1 wherein said general purpose computer is an Intel Pentium® processor based computer and said general purpose operating system is a Microsoft Windows NT®.

15. The control system according to claim 1 wherein the mechanical actuator is a servo motor and said control algorithm is a servo control algorithm.

16. The control system according to claim 1 wherein said robot move module includes a kinematics model for calculating a required joint position in response to a move command.

17. A versatile robot control system suitable for controlling robots of different electromechanical configurations, the control system comprising:
   a robot-independent computer unit including a video display and a first digital processor running an operator interface module for creating a sequence of robot move commands; and a robot-specific controller unit operably linked to the robot and including a second digital processor running a real-time tied operating system and a robot move module for executing said robot move commands, said robot specific controller unit being in electronic communication with said robot independent computer unit.

18. The control system according to claim 17 wherein said general-purpose computer and said real-time computer subsystem are electronically linked via a standard data bus.

19. The control system according to claim 17 wherein said first digital processors runs an operator interface module including:

a configuration variable for storing data specifying the electromechanical configuration of the robot;

a first code segment for generating a first operator display according to a first electromechanical configuration;

a second code segment for generating a second operator display according to a second electromechanical configuration; and a third code segment for selecting said first or second code segment according to said electromechanical configuration.

20. The control system according to claim 19 wherein said first code segment generates an operator display requesting operating limits for a revolute joint.

21. The control system according to claim 19 wherein said second code segment generates an operator display requesting operating limits for a linear joint.

22. The control system of claim 19 wherein said configuration variable is defined to store data specifying a robot joint type.

23. The control system of claim 19 wherein said configuration variable is defined to store data specifying a linear joint type.

24. The control system of claim 19 wherein said configuration variable is defined to store data specifying a revolute joint type.

25. The control system of claim 19 wherein said configuration variable is defined to store data specifying whether a robot joint is windable.

26. An operator interface module for controlling robots of different electromechanical configurations, the operator interface module comprising:

a first code segment for generating a first operator display according to a first electromechanical configuration;

a second code segment for generating a second operator display according to a second electromechanical configuration; and a third segment for selecting said first or second code segment according to said electromechanical configuration.

27. The operator interface according to claim 26 wherein said first code segment generates an operator display requesting operating limits for a revolute joint.

28. The operator interface according to claim 26 wherein said second code segment generates an operator display requesting operating limits for a linear joint.

29. The operator interface module of claim 26 wherein said configuration variable is defined to store data specifying a robot joint type.

30. The operator interface module of claim 26 wherein said configuration variable is defined to store data specifying a linear joint type.

31. The operator interface module of claim 26 wherein said configuration variable is configured to store data specifying a revolute joint type.

32. The operator interface module of claim 26 wherein said configuration variable is defined to store data specifying whether a robot joint is windable.

* * * * *